United States Patent
Sugiyama et al.

(10) Patent No.: US 9,387,228 B2
(45) Date of Patent: Jul. 12, 2016

(54) AGENT FOR PREVENTION OR AMELIORATION OF OBESITY

(71) Applicant: HIROSHIMA UNIVERSITY, Higashi-Hiroshima-shi (JP)

(72) Inventors: Masanori Sugiyama, Hiroshima (JP); Fumiko Higashikawa, Hiroshima (JP); Masafumi Noda, Hiroshima (JP)

(73) Assignee: HIROSHIMA UNIVERSITY, Higashi-Hiroshima-shi (JP)

( * ) Notice: Subject to any disclaimer, the term of this patent is extended or adjusted under 35 U.S.C. 154(b) by 7 days.

(21) Appl. No.: 14/327,893

(22) Filed: Jul. 10, 2014

(65) Prior Publication Data

US 2014/0322186 A1  Oct. 30, 2014

Related U.S. Application Data

(62) Division of application No. 13/203,523, filed as application No. PCT/JP2010/001334 on Feb. 26, 2010, now abandoned.

(30) Foreign Application Priority Data

Feb. 27, 2009 (JP) ................................. 2009-046388

(51) Int. Cl.
  *C12N 1/00* (2006.01)
  *A61K 35/74* (2015.01)
  *A23L 1/30* (2006.01)

(52) U.S. Cl.
  CPC ............... *A61K 35/74* (2013.01); *A23L 1/3014* (2013.01); *A23V 2002/00* (2013.01)

(58) Field of Classification Search
  CPC ............. C12N 1/20; C12R 1/01; A61K 35/74
  See application file for complete search history.

(56) References Cited

U.S. PATENT DOCUMENTS

| 4,877,615 | A | 10/1989 | Vandenbergh et al. |
| 5,968,569 | A | 10/1999 | Cavadini et al. |
| 7,098,029 | B1 | 8/2006 | Belyea et al. |
| 2002/0037577 | A1 | 3/2002 | Park et al. |
| 2003/0180271 | A1 | 9/2003 | Park et al. |
| 2003/0180273 | A1 | 9/2003 | Park et al. |
| 2005/0112112 | A1 | 5/2005 | Park et al. |
| 2005/0130288 | A1* | 6/2005 | Choi ............... A23K 1/003 435/243 |
| 2006/0233777 | A1* | 10/2006 | Piva ............... A61K 38/164 424/94.2 |
| 2007/0286916 | A1* | 12/2007 | Bengmark ........... A61K 31/198 424/780 |
| 2010/0021445 | A1 | 1/2010 | Kawakami et al. |
| 2010/0129333 | A1 | 5/2010 | Kawakami et al. |

FOREIGN PATENT DOCUMENTS

| JP | 63 295511 | 12/1988 |
| JP | 2008 24680 | 2/2008 |
| JP | 2008-156299 A | 7/2008 |
| JP | 2008156299 | 7/2008 |
| JP | 2008 178398 | 8/2008 |
| JP | 2008 214253 | 9/2008 |
| WO | WO 01/33977 A1 | 5/2001 |
| WO | WO 01/88095 A1 | 11/2001 |

OTHER PUBLICATIONS

Minamida, K. et al., Shokuhin to Gijutsu, pp. 1-7, (May 25, 2005).
Cho, S-Y. et al., "Revovery of Vegetable Lactic Acid Bacterium Effective for Preventing and Ameliorating Metabolic Syndrome and Analysis of Physiological Function of the Bacterium" 129th Annual Convention, The Pharmaceutical Society of Japan, 27H-AM15, p. 74, (Mar. 5, 2009).
International Search Report Issued Apr. 6, 2010 in PCT/JP10/001334 filed Feb. 26, 2010.
Extended European Search Report issued Mar. 4, 2013, in European Patent Application No. 10746014.9.
Hekui Jin, et al., "Establishment of an in Vitro Peyer's Patch Cell Culture System Correlative to in Vivo Study Using Intestine and Screening of Lactic Acid Bacteria Enhancing Intestinal Immunity", Biol. Pharm. Bull., vol. 33, No. 2, XP-055053871, Feb. 2010, pp. 289-293.
Xingrong Zhao, et al., "The Obesity and Fatty Liver are Reduced by Plant-Derived Pediococcus pentosaceus LP28 in High Fat Diet-Induced Obese Mice", Plos One, vol. 7, No. 2, XP-055053837, Feb. 2012, 8 pages.

* cited by examiner

*Primary Examiner* — Ruth Davis
(74) *Attorney, Agent, or Firm* — Oblon, McClelland, Maier & Neustadt, L.L.P

(57) ABSTRACT

To provide a pharmaceutical product or food which has an excellent fat-accumulation-inhibiting activity and/or fat-metabolism-improving activity and which is effective for inhibition or improvement of obesity, fatty liver, etc. The present invention provides an agent for preventing or ameliorating obesity containing, as an active ingredient, cells of a lactic acid bacterium belonging to the genus *Pediococcus*, a cell culture thereof, or an extract of any of these.

2 Claims, 3 Drawing Sheets

AGENT FOR PREVENTION OR AMELIORATION OF OBESITY

CROSS-REFERENCE TO RELATED APPLICATIONS

This application is a divisional of U.S. application Ser. No. 13/203,523 filed Aug. 26, 2011, pending, which is a National Stage of PCT/JP10/001334 filed Feb. 26, 2010 and claims the benefit of JP 2009-046388 filed Feb. 27, 2009.

TECHNICAL FIELD

The present invention relates to an agent for preventing or ameliorating obesity containing, as an active ingredient, cells of a lactic acid bacterium, a culture thereof, etc. and to products related thereto.

BACKGROUND ART

Obesity is defined as a condition in which energy sources such as carbohydrates and lipids have been over-accumulated as neutral fat in white adipocytes which are present in the living tissue, particularly in the subcutaneous adipose tissue or in the organ-peripheral tissue, resulting in an increase in body weight beyond the limits of skeletal systems or physiological functions. Among fat tissues, a visceral fat tissue, which builds up around an internal organ such as the mesentery, is thought to trigger abnormality in metabolism of carbohydrate or lipid, possibly resulting in lifestyle-related diseases such as heart diseases, arteriosclerosis, hypertension, diabetes, and fatty liver. When the aforementioned visceral-fat-induced obesity is associated with a plurality of arteriosclerosis risk factors including diabetes (carbohydrate metabolic disorder), hyperlipidemia (lipid metabolic disorder), and hypertension, such a condition is called metabolic syndrome. In metabolic syndrome, even when individual symptoms are not so severe, combination of a plurality of symptoms synergistically elevate possibility of onset of lifestyle-related diseases. Thus, metabolic syndrome patients are categorized into a high-risk group, and prevention and therapy of metabolic syndrome have been focused on.

As described above, accumulation of visceral fat is thought to be a considerably important factor for the onset of metabolic syndrome, lipid metabolic disorders (e.g., fatty liver and hyperlipidemia), carbohydrate metabolic disorders (e.g., diabetes), and cardiovascular diseases such as heart infarction and brain infarction. Therefore, for preventing or ameliorating these disease and pathological conditions, it is important to reduce accumulation of visceral fat.

Measures that have been proposed for preventing obesity include control of metabolism of lipid taken into the body, promoting burning of body fat, intake of a food or supplement which inhibits accumulation of fat, and administration of an anti-obesity agent in the medical field have been proposed. However, currently, there is only a few means to be effective for preventing and ameliorating obesity, from the aspect of safety and practical utility (e.g., satisfactory taste or processability).

Meanwhile, lactic acid bacteria have been used for many years in production of food, particularly milk products such as fermented milk, lactic acid bacterium beverage, and fermented butter. In addition, since lactic acid bacteria themselves have a variety of pharmacological activities including intestinal function control action, the lactic acid bacteria are used as materials for producing health food products, pharmaceutical products, etc. In previous reports of activity of lactic acid bacteria on fat accumulation, those belonging to genus *Lactobacillus* or the genus *Lactococcus* have been found to have a visceral-fat-reducing activity (Patent Document 1), and those belonging to the genus *Lactobacillus gasseri* have been found to have a fatty-liver-inhibitory action (Patent Document 2).

However, a lactic acid bacterium belonging to the genus *Pediococcus* has never been known to have a fat-accumulation-inhibiting activity and/or a fat-metabolism-improving activity.

PRIOR ART DOCUMENTS

Patent Documents

Patent Document 1: JP-A-2008-214253
Patent Document 2: JP-A-2008-24680

SUMMARY OF THE INVENTION

Problems to be Solved by the Invention

An object of the present invention is to provide a pharmaceutical product or food which has an excellent fat-accumulation-inhibitory action and/or fat-metabolism-improving action and which is effective for inhibition or improvement of obesity, fatty liver, etc.

Means for Solving the Problems

The present inventors have carried out extensive studies on the pharmacological activity of lactic acid bacteria, and have found that lactic acid bacteria belonging to the genus *Pediococcus* have a fat-accumulation-inhibitory action and a lipid-metabolic-disorder-improving activity. The present invention has been accomplished on the basis of this finding.

Accordingly, the present invention is directed to the following (1) to (10):

(1) an agent for preventing or ameliorating obesity containing, as an active ingredient, cells of a lactic acid bacterium belonging to the genus *Pediococcus*, a cell culture thereof, or an extract of any of these;

(2) a fat-accumulation-inhibiting agent containing, as an active ingredient, cells of a lactic acid bacterium belonging to the genus *Pediococcus*, a cell culture thereof, or an extract of any of these;

(3) a fat-metabolism-improving agent containing, as an active ingredient, cells of a lactic acid bacterium belonging to the genus *Pediococcus*, a cell culture thereof, or an extract of any of these;

(4) a food for preventing or ameliorating obesity containing cells of a lactic acid bacterium belonging to the genus *Pediococcus*, a cell culture thereof, or an extract of any of these;

(5) an agent for preventing or ameliorating obesity according to (1), a fat-accumulation-inhibiting agent according to (2), a fat-metabolism-improving agent according to (3), or a food according to (4), wherein the lactic acid bacterium belonging to the genus *Pediococcus* is *Pediococcus pentosaceus* LP28 strain, which has been deposited as NITE ABP-700 at the National Institute of Technology and Evaluation, Patent Microorganisms Depositary;

(6) *Pediococcus pentosaceus* LP28 strain, which has been deposited as NITE ABP-700 at the National Institute of Technology and Evaluation, Patent Microorganisms Depositary;

(7) use of cells of a lactic acid bacterium belonging to the genus *Pediococcus*, a cell culture thereof, or an extract of any of these, for producing an agent for preventing or ameliorating obesity;

(8) use of cells of a lactic acid bacterium belonging to the genus *Pediococcus*, a cell culture thereof, or an extract of any of these, for producing a fat-accumulation-inhibiting agent;

(9) use of cells of a lactic acid bacterium belonging to the genus *Pediococcus*, a cell culture thereof, or an extract of any of these, for producing a fat-metabolism-improving agent; and

(10) a method for preventing or ameliorating obesity, characterized in that the method comprises administering, to a subject in need thereof, cells of a lactic acid bacterium belonging to the genus *Pediococcus*, a cell culture thereof, or an extract of any of these, or allowing a subject in need thereof to consume cells of a lactic acid bacterium belonging to the genus *Pediococcus*, a cell culture thereof, or an extract of any of these.

Effects of the Invention

The agent for preventing or ameliorating obesity, fat-accumulation-inhibiting agent, and fat-metabolism-improving agent according to the present invention can be used as a pharmaceutical product, a food, etc. for preventing, treating, or ameliorating lipid metabolic disorders (e.g., fatty liver and hyperlipidemia), carbohydrate metabolic disorders (e.g., diabetes), and cardiovascular diseases such as heart infarction and brain infarction. In addition, the lactic acid bacterium belonging to the genus *Pediococcus* can be provided on a large scale at low cost, has high safety, and can be administered for a long period of time. Thus, the lactic acid bacterium of the present invention is remarkably useful.

MODES FOR CARRYING OUT THE INVENTION

Figure 1:
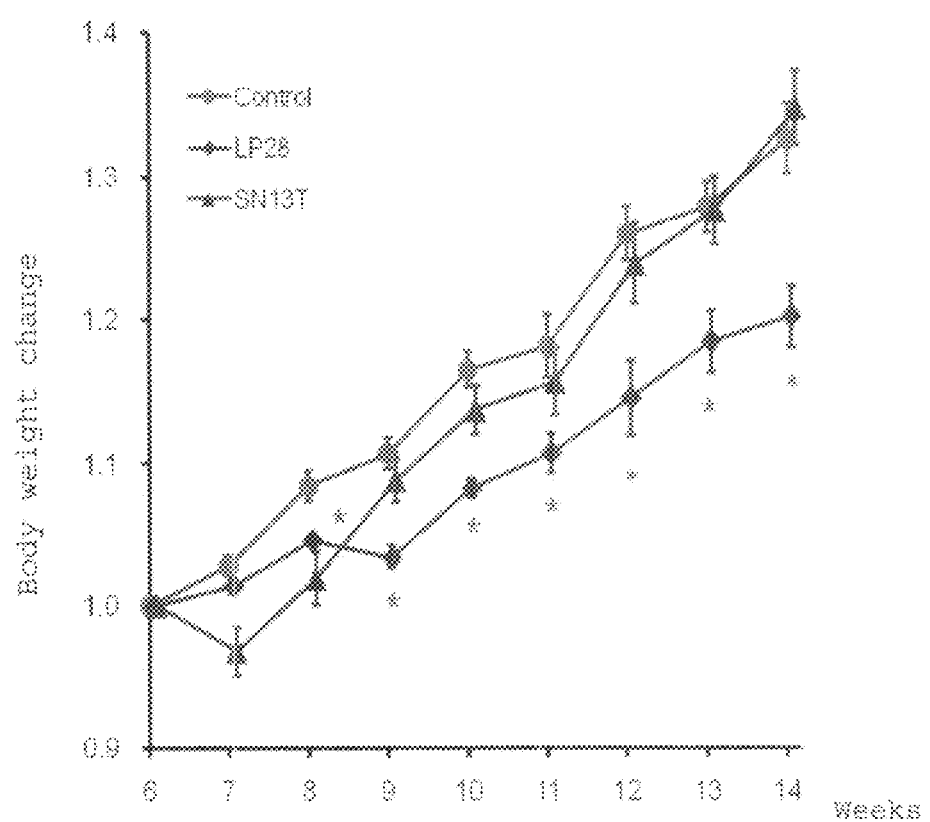
FIG. 1: A graph showing body weight change profiles under intake of high-fat food.

The lactic acid bacterium employed in the agent of the present invention for preventing or ameliorating obesity is a lactic acid bacterium belonging to the genus *Pediococcus*.

No particular limitation is imposed on the lactic acid bacterium belonging to the genus *Pediococcus*, so long as the lactic acid bacterium exhibits the effects of the present invention. Examples of the lactic acid bacterium of the present invention include *Pediococcus pentosaceus, Pediococcus damnosus, Pediococcus urinaeequi, Pediococcus cerevisiae,* and *Pediococcus halophilus*. Among such bacteria, preferred is a lactic acid bacterium belonging to the genus *Pediococcus* which exhibits high viability in the human intestinal tract and, in food products produced therefrom, which exhibits high percent survival and provides excellent flavor and texture.

Among them, *Pediococcus pentosaceus* is more preferred. *Pediococcus pentosaceus* LP28 strain, which has been deposited as NITE ABP-700 (Date of original deposit: Jan. 27, 2009) at the National Institute of Technology and Evaluation, Patent Microorganisms Depositary (2-5-8, Kazusakamatari, Kisarazu City, Chiba 292-0818 JAPAN), is even more preferred.

The LP28 strain has been first isolated from the fruit of *Longan* by the present inventors. The nucleotide sequence of 16S rDNA of the LP28 strain has a homology of 99.5% to that of *Pediococcus pentosaceus* ATCC 25745 strain (DDBJ/GenBank/EMBL ID=FM179610). The LP28 strains exhibits a tetragena profile under microscope after Gram staining. Therefore, the LP28 strain has been identified as *Pediococcus pentosaceus*. The LP28 strain has the following general mycological characteristics:

(1) Gram-positive *lactococcus*, (2) homo-type lactic fermentation, 3) catalase negative, (4) no endospore formability, (5) culturable under aerobic conditions, and (6) producing exopolysaccharide.

In the present invention, cells of the lactic acid bacterium which have been recovered by culturing the bacterium through a customary method for cultivating a lactic acid bacterium and separating cells thereof from the culture by cell-collecting means such as centrifugation may be used without performing further treatment. Alternatively, a culture/fermentation liquid (culture supernatant), a concentration thereof, or a cytoplasm fraction or a cell wall fraction obtained through treatment of cells of the bacterium with an enzyme or by physical means, may also be used. The cells may be viable cells or killed cells.

No particular limitation is imposed on the medium in which the lactic acid bacterium of the present invention is cultured, and there may be employed a variety of media such as a fruit juice medium, a vegetable juice medium, a milk medium, a skimmed milk medium, a medium containing a milk component, and a semi-synthetic medium free of a milk component. Specific examples of the culture medium include a reduced skimmed milk medium produced through heat-sterilized skimmed milk; a skimmed milk medium to which yeast extract has been added; an MRS medium; and a GAM medium.

No particular limitation is imposed on the culturing method, so long as the method allows favorable growth of the target cells. Examples of the method include stationary culture, neutralization culture (at a constant pH), batch culture, and continuous culture.

In the culturing, sake cake, a distillation residue obtained in the production of sho-chu, or an extract thereof is preferably added to the culture medium. Particularly in the case of producing fermented milk, fermented fruit juice, or fermented vegetable juice, such an additive is preferably used, since a favorable fermentation product can be obtained.

In the present invention, the cells of a lactic acid bacterium belonging to the genus *Pediococcus* or the extract of the cell culture of the bacterium refers to various solvent-extracts obtained through solvent extraction of cells of the bacterium or the cell culture thereof, a dilution product thereof, a concentration product thereof, or a dry powder thereof.

The extraction solvent for use in recovering the extract of the present invention may be either a polar solvent, a non-polar solvent, or a mixture thereof. Examples of the solvent include water; alcohols such as methanol, ethanol, propanol, and butanol; polyhydric alcohols such as propylene glycol and butylene glycol; ketones such as acetone and methyl ethyl ketone; esters such as methyl acetate and ethyl acetate; linear or cyclic ethers such as tetrahydrofuran and diethyl ether; polyethers such as polyethylene glycol; hydrocarbons such as hexane, cyclohexane, and petroleum ether; aromatic hydrocarbons such as benzene and toluene; and pyridines. Among them, esters such as ethyl acetate and alcohols such as ethanol are preferred.

Extraction conditions vary in accordance with the type of solvent. In one preferred extraction procedure, a solvent (1 to 10 parts by mass) is used with respect to 1 part by mass of culture liquid, and extraction is performed at 0 to 50° C., preferably 25 to 37° C., for 0.5 hours to 3 hours.

The aforementioned extract may be used as is. Alternatively, the extract may be diluted, concentrated, or lyophilized, and the product may be formed into powder or paste, as desired. Through a purification technique such as liquid-liquid partition, the extract may be appropriately purified before use.

As described in the Examples hereinbelow, the cells of a lactic acid bacterium belonging to the genus *Pediococcus* of the present invention can inhibit body weight increase in a hypernutrition state and can reduce the weight of white adipocyte tissue and the liver neutral fat (triglyceride) level. Thus, cells of a lactic acid bacterium belonging to the genus *Pediococcus*, a cell culture thereof, or an extract of any of these can serve as an agent for preventing or ameliorating obesity, a fat-accumulation-inhibiting agent, or a lipid-metabolism-improving agent. That is, cells of a lactic acid bacterium belonging to the genus *Pediococcus*, a cell culture thereof, or an extract of any of these can be employed as a food, pharmaceutical product, or the like which can effectively prevent, treat, or ameliorate pathological conditions triggered by accumulation of body fat and/or lipid metabolic disorder; i.e., obesity, lipid metabolic disorders (e.g., fatty liver and hyperlipidemia), and carbohydrate metabolic disorders (e.g., diabetes), or which can effectively prevent, treat, or ameliorate cardiovascular diseases such as heart infarction and brain infarction. When the bacterium is employed for providing a food, the food may have a product concept of prevention or amelioration of obesity, a healthy diet, etc. and may serve as a functional food (e.g., a beauty food, patient diet, or food for specified health uses) optionally having a label indicating such effects.

The agent for preventing or ameliorating obesity, fat-accumulation-inhibiting agent, or lipid-metabolism-improving agent of the present invention may be perorally or parenterally administered as a pharmaceutical product or a supplement. In peroral administration, a tablet, a capsule, a granule, a powder, a syrup, etc. may be employed. In parenteral administration, an injection, a suppository, an inhalation, a percutaneous agent, a drug for external use, etc. may be employed. In the preparation of various forms of the aforementioned pharmaceutical preparations and supplements, additional pharmaceutically acceptable carries may be appropriately used in combination, so long as the effects of the bacterial cells or culture of the present invention are not impaired. Examples of such carriers include a vehicle, a binder, a bulking agent, a disintegrator, a surfactant, a lubricant, a dispersant, a buffer, a preservative, a flavoring agent, a perfume, a coating agent, a carrier, and a diluent.

Among the administration routes, peroral administration is preferred. When the bacterium of the present invention is used as a peroral preparation, the preparation has a fat content of 0.1 mass % to 100 mass % with respect to the total amount of the preparation, preferably 1 mass % to 100 mass %.

The agent for preventing or ameliorating obesity, fat-accumulation-inhibiting agent, or lipid-metabolism-improving agent of the present invention may be employed as a variety of food products. Examples of the form thereof include beverages such as fruit juice, vegetable juice, sparkling drink, tea beverage, milk beverage, fermented milk, fermented fruit juice, fermented vegetable juice, alcoholic beverages, and refreshing beverages; other foods such as jelly-like foods, snack foods, baked cakes, cakes, chocolate, jam, bread, gum, candy, soup, pickles, and tsukuda-ni; and the same as the aforementioned forms in relation to the peroral preparation (tablet, capsule, syrup, etc.).

The culture product of the lactic acid bacterium belonging to the genus *Pediococcus* of the present invention serves, without any further treatment, as a fermented food such as yogurt, cheese, miso, shoyu, or pickles. By use of such fermented milk or cheese as raw material, bread, snack food, cakes, etc. for the concept of reducing visceral fat may be provided.

No particular limitation is imposed on the amount of the lactic acid bacterium of the present invention incorporated into the pharmaceutical product or food, and the bacterium content may be appropriately adjusted in accordance with the daily dose or other factors. In the case of liquid preparations, the lactic acid bacterium content is preferably adjusted to $1 \times 10^8$ cells/mL to $1 \times 10^{10}$ cells/mL. In the case of solid preparations, the bacterium content is preferably adjusted to $1 \times 10^8$ cells/g to $1 \times 10^{10}$ cells/g.

When viable cells of the lactic acid bacterium of the present invention belonging to the genus *Pediococcus* are administered, the daily dose thereof for an adult is preferably $1 \times 10^{12}$ to $5 \times 10^{13}$ cfu/day.

The present invention will next be described in more detail by way of Examples and Test Examples.

EXAMPLES

Production Example 1

Preparation of Cells of a Lactic Acid Bacterium

An MRS medium (product of Merck) was sterilized at 118° C. for 15 minutes. To the culture medium, *Pediococcus pentosaceus* LP28 strain (deposited as NITE ABP-700 (Date of original deposit: Jan. 27, 2009) at the National Institute of Technology and Evaluation, Patent Microorganisms Depositary (2-5-8, Kazusakamatari, Kisarazu City, Chiba 292-0818 JAPAN) was inoculated. The thus-inoculated cells were cultured at 28° C. for 36 hours under anaerobic conditions. The resulting culture product was washed thrice with PBS and lyophilized, to thereby recover a cell powder of LP28 strain. The cell powder was stored at −80° C. before experiments. In a similar manner, *Lactobacillus plantarum* SN13T strain (NITE P-7), obtained from sausage, was cultured, to thereby recover a cell powder of SN13T strain, as a comparative strain sample.

Test Example 1

(1) Test Method

A high-fat diet (D12492-Rodent Diet with 60 kcal % Fat, Research Diets Inc., New Brunswick, N.J.) was fed to 7-week-old to 8-week-old mice (BALB/c) over 6 weeks, to thereby trigger obesity. In the subsequent 8 weeks, the same high-fat diet was fed to the mice with or without intake of a cell powder of LP28 strain or a cell powder of SN13T strain, prepared in Production Example 1. The body weight of each mouse was monitored. Also, 8 weeks after start of intake of each bacterium, the weight of white adipose tissue in the abdominal cavity of each mouse and the amount of liver neutral fat thereof were measured.

The amount of liver neutral fat was determined by removing the liver from the mouse, suspending the liver in chloroform/methanol (2:1), shaking the suspension, and determining the triglyceride level of the chloroform layer (Triglyceride E-Test Wako for triglyceride level determination, product of Wako Pure Chemical Industries, Ltd.).

In intake of the cell powder of LP28 strain or the cell powder of SN13T strain, each cultured product of the cells was added to a crumbled feed (25 mg/1 g-crumbled feed), and mice (5 mice in each group) were allowed to take the chaw ad libitum. No difference was observed in consumption of the feed among the lactic acid bacterium-free group, LP28-intake group, and SN13T-intake group, and the daily consumption was about 2.5 g/mouse.

(2) Results

Figure 2:
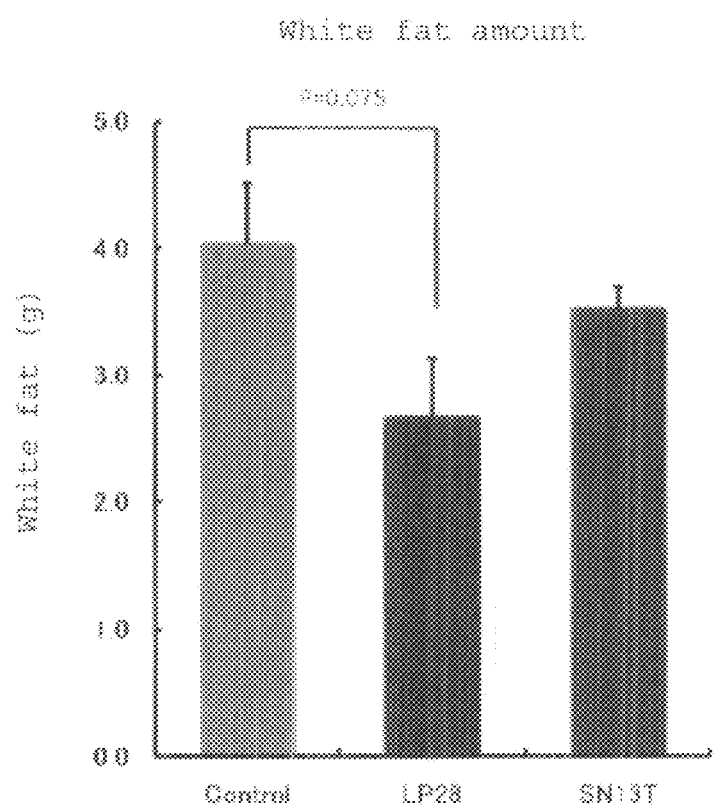
FIG. 2: A graph showing the weights of white adipocytes under intake of high-fat food.
Figure 3:
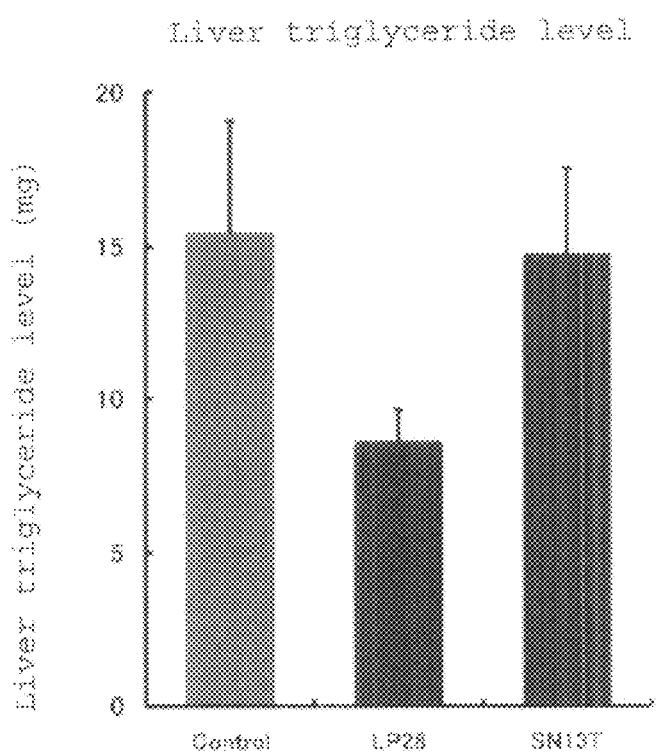
FIG. 3: A graph showing the liver neutral fat (triglyceride) levels under intake of high-fat food.

In the LP28-intake group, the body weight increase attributed to intake of the high-fat diet was significantly inhibited ($P<0.05$), as compared with the lactic acid bacterium-free group. In contrast, no difference in body weight was observed between the SN13T-intake group and the lactic acid bacterium-free group (FIG. 1). In the LP28-intake group, the white adipose tissue weight (FIG. 2), the liver weight, and the liver neutral fat level (FIG. 3) in intake of the high-fat diet were reduced.

Thus, since LP28 exhibited effects of inhibiting increases in body weight and fat and fat liver in a hypernutrition state, the strain is thought to be effective for preventing or ameliorating metabolic syndrome.

Test Example 2

Variation in Gene Expression in the Liver

Among the test animals of Test Example 1, one mouse was chosen from each of the LP28-intake group and the lactic acid bacterium-free group, and total RNA was extracted from the liver of each mouse. The liver sample was subjected to cDNA microarray analysis (Affymetrix).

As a result, variation of expression of a variety of fat-related genes, including very low density lipoprotein receptor, CD36 antigen, peroxisome proliferator activated receptor gamma (PPARγ), stearoyl-coenzyme A desaturase 1, sterol regulatory element binding transcription factor 1 (SREBF1), and fatty acid synthase, was observed.

Example 1

Production of Fermented Milk

Cells of *Pediococcus pentosaceus* LP28 strain (NITE ABP-700) were cultivated at 30° C. for 20 hours in a medium containing 100% from-concentrate pear juice, 1.0% sodium citrate, and 1.0% sho-chu distillation residue extract, to thereby prepare a preliminary culture liquid. Separately, 1% sho-chu distillation residue extract was added to 13% skimmed milk (product of Meiji Dairies Corporation). The mixture was sterilized at 121° C. for 15 minutes and then cooled to 30° C., to thereby yield a main culture medium. The above-produced preliminary culture liquid was inoculated (2%) to the main culture medium, and cultivation was performed at 30° C. for 24 hours, to thereby produce fermented milk (lactic acid acidity: 0.59%).

Example 2

Production of Fermented Vegetable Juice

Cells of *Pediococcus pentosaceus* LP28 strain (NITE ABP-700) were cultivated at 30° C. for 20 hours in a medium containing 100% from-concentrate pear juice, 1.0% sodium citrate, and 1.0% sho-chu distillation residue extract, to thereby prepare a preliminary culture liquid. Separately, 0.1% skimmed milk and 0.8% sho-chu distillation residue extract were added to 100% from-concentrate carrot juice. The mixture was sterilized at 105° C. for 5 minutes and then cooled to 30° C., to thereby yield a carrot juice culture medium. The above-produced preliminary culture liquid was inoculated (2%) to the carrot juice culture medium, and cultivation was performed at 30° C. for 24 hours, to thereby produce fermented carrot juice (lactic acid acidity: 0.61%).

The invention claimed is:
1. A method for treating obesity, comprising administering, to a subject in need thereof, a food composition comprising cells of *Pediococcus pentosaceus* LP28 strain, which has been deposited as NITE ABP-700 at the National Institute of Technology and Evaluation, Patent Microorganisms Depositary, or a cell culture thereof.
2. The method according to claim 1, wherein the cells are administered in an amount of $1\times10^{12}$ to $5\times10^{13}$ cfu/day for a human adult.

* * * * *